United States Patent
Bui et al.

(10) Patent No.: US 7,091,259 B2
(45) Date of Patent: *Aug. 15, 2006

(54) DENTAL FILLERS, PASTES, AND COMPOSITIONS PREPARED THEREFROM

(75) Inventors: Hoa T. Bui, Mendota Heights, MN (US); Brant U. Kolb, Afton, MN (US); Sumita B. Mitra, West St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 380 days.

This patent is subject to a terminal disclaimer.

(21) Appl. No.: 10/190,321

(22) Filed: Jul. 3, 2002

(65) Prior Publication Data

US 2004/0010055 A1    Jan. 15, 2004

(51) Int. Cl.
 A61K 6/083    (2006.01)
 C08K 9/06    (2006.01)
 A61C 5/00    (2006.01)

(52) U.S. Cl. .................. 523/115; 523/116; 523/118; 523/120; 523/212; 523/214; 524/450; 106/35; 427/220; 428/405; 433/228.1

(58) Field of Classification Search ............... 523/115, 523/116, 118, 120, 212, 214; 524/450; 106/35; 427/220; 428/405

See application file for complete search history.

(56) References Cited

U.S. PATENT DOCUMENTS

| | | |
|---|---|---|
| 3,066,112 A | 11/1962 | Bowen |
| 3,539,533 A | 11/1970 | Lee II et al. |
| 3,629,187 A | 12/1971 | Waller |
| 3,655,605 A | 4/1972 | Smith |
| 3,708,296 A | 1/1973 | Schlesinger |
| 3,709,866 A | 1/1973 | Waller |
| 3,751,399 A | 8/1973 | Lee, Jr. et al. |
| 3,766,132 A | 10/1973 | Lee, Jr. et al. |
| 3,814,717 A | 6/1974 | Wilson et al. |
| 3,860,556 A | 1/1975 | Taylor |
| 4,002,669 A | 1/1977 | Gross et al. |
| 4,043,327 A | 8/1977 | Potter et al. |
| 4,069,055 A | 1/1978 | Crivello |
| 4,071,424 A | 1/1978 | Dart et al. |
| 4,115,346 A | 9/1978 | Gross et al. |
| 4,143,018 A | 3/1979 | Crisp et al. |
| 4,209,434 A | 6/1980 | Wilson et al. |
| 4,216,288 A | 8/1980 | Crivello |
| 4,250,311 A | 2/1981 | Crivello |
| 4,259,117 A | 3/1981 | Yamauchi et al. |
| 4,292,029 A | 9/1981 | Craig et al. |
| 4,308,190 A | 12/1981 | Walkowiak et al. |
| 4,327,014 A | 4/1982 | Kawahara et al. |
| 4,379,695 A | 4/1983 | Orlowski et al. |
| 4,387,240 A | 6/1983 | Berg |
| 4,404,150 A | 9/1983 | Tsunekawa et al. |
| 4,642,126 A | 2/1987 | Zador et al. |
| 4,652,274 A | 3/1987 | Boettcher et al. |
| 4,673,354 A | 6/1987 | Culler |
| 4,737,593 A | 4/1988 | Ellrich et al. |
| 4,772,530 A | 9/1988 | Gottschalk et al. |
| 4,872,936 A | 10/1989 | Engelbrecht |
| 4,874,450 A | 10/1989 | Gottschalk |
| 4,954,414 A | 9/1990 | Adair et al. |
| 4,985,340 A | 1/1991 | Palazotto et al. |
| 5,055,372 A | 10/1991 | Shanklin et al. |
| 5,057,393 A | 10/1991 | Shanklin et al. |
| 5,063,257 A | 11/1991 | Akahane et al. |
| 5,084,586 A | 1/1992 | Farooq |
| 5,089,536 A | 2/1992 | Palazzotto |
| 5,124,417 A | 6/1992 | Farooq |
| 5,130,347 A | 7/1992 | Mitra |
| 5,154,613 A | 10/1992 | Cohen |
| 5,154,762 A | 10/1992 | Mitra et al. |
| 5,332,429 A | 7/1994 | Mitra et al. |
| 5,453,456 A | 9/1995 | Mitra et al. |
| 5,520,725 A | 5/1996 | Kato et al. |
| 5,545,676 A | 8/1996 | Palazzotto et al. |
| 5,552,485 A | 9/1996 | Mitra et al. |
| 5,670,258 A | 9/1997 | Mitra et al. |
| 5,856,373 A | 1/1999 | Kaisaki et al. |
| 5,883,153 A | 3/1999 | Roberts et al. |
| 5,910,471 A * | 6/1999 | Christianson et al. ......... 51/295 |
| 5,958,794 A | 9/1999 | Bruxvoort et al. |
| 6,020,528 A | 2/2000 | Leppard et al. |
| 6,025,406 A | 2/2000 | Oxman et al. |

(Continued)

FOREIGN PATENT DOCUMENTS

EP    0 173 567 A2    2/1986

(Continued)

OTHER PUBLICATIONS

American National Standard/American Dental Association (ADA); Specification No. 27; "Resin Based Filling Materials;" ADA, Chicago, IL; 36 pgs. (Jul. 16, 1993).

(Continued)

*Primary Examiner*—Tae H. Yoon
(74) *Attorney, Agent, or Firm*—Sean J. Edman

(57) ABSTRACT

The present invention provides a dental paste, methods of making and using the dental paste, and compositions prepared therefrom. The dental paste includes (a) a filler including porous, non-pyrogenic silica having a silane treated surface and being substantially free of heavy metals and (b) a filler including non-agregated primary silica particles, with the fillers being dispersed in a hardenable resin. Fillers including porous, non-pyrogenic silica, and methods of making and using the fillers, are also provided.

40 Claims, No Drawings

U.S. PATENT DOCUMENTS

| | | | |
|---|---|---|---|
| 6,297,181 B1 | 10/2001 | Kunert et al. | |
| 6,376,590 B1 | 4/2002 | Kolb et al. | |
| 6,384,107 B1 * | 5/2002 | Liu | 523/118 |
| 6,387,981 B1 | 5/2002 | Zhang et al. | |
| 6,583,208 B1 * | 6/2003 | Suzuki | 524/445 |
| 6,613,812 B1 * | 9/2003 | Bui et al. | 523/116 |
| 2002/0129736 A1 | 9/2002 | Bui et al. | |
| 2002/0156152 A1 | 10/2002 | Zhang et al. | |

FOREIGN PATENT DOCUMENTS

| | | |
|---|---|---|
| EP | 0 323 120 A2 | 7/1989 |
| EP | 0 323 120 A3 | 7/1989 |
| EP | 0 323 120 B1 | 3/1994 |
| GB | 2 108 132 A | 5/1983 |
| WO | WO 01/30304 A1 | 5/2001 |
| WO | WO 01/30306 A1 | 5/2001 |
| WO | WO 01/30307 A1 | 5/2001 |
| WO | WO 02/053107 | 7/2002 |

OTHER PUBLICATIONS

ISO 4049 International Standard; "Dentistry—Polymer-based filling, restorative and luting materials;" International Organization for Standardization, Geneva, Switzerland; Title page, Publication page, Table of Contents, and pp. 1-27 (33 pgs. total) (Jul. 15, 2000).

Material Safety Data Sheet, OSi Specialties A Crompton Business, Product Name: Silquest A-1230 silane, MSDS # 1519, Revision: 1.2; Crompton Corporation, Greenwich, CT; 9 pgs.(Jul. 5, 2000).

Revised American National Standard/American Dental Association (ADA); Specification No. 9 for Dental Silicate Cement; ADA, Chicago, IL; 17 pgs. (Jun. 30, 1980).

*Grant & Hackh's Chemical Dictionary*, 5th Edition, Roger and Claire Grant, Eds., McGraw-Hill Book Company, New York, NY (1987), Title page, Publication page, and pp. 529-531 (5 pgs total).

* cited by examiner

DENTAL FILLERS, PASTES, AND COMPOSITIONS PREPARED THEREFROM

BACKGROUND

Acid-reactive fillers have been widely used in dental compositions. Acid-reactive fillers include, for example, metal oxides, metal salts, and glasses. An example of an acid-reactive glass is fluoroalumuniosilicate (FAS) glass, which is a known fluoride releasing material. It is known in the art to coat or surface treat acid-reactive fillers with various substances to enhance desired properties.

For example, metal oxide powders (e.g., calcium oxide and aluminum oxide) have been coated with water-soluble high molecular weight (MW) substances to reportedly increase crushing strength, hydrophilicity, and working time, and to decrease solubility; calcium aluminum fluorosilicate glass has been treated with an acid to reportedly reduce water sensitivity and extend setting time; aluminoborate glass used in a cement has been washed with ammonium phosphate to reportedly extend the setting time of the cement; and fluoroaluminosilicate glass has been treated with silanes and/or silanols to reportedly provide cements with improved diametral tensile strength and improved fracture toughness.

For some applications, it is preferred to disperse the acid-reactive filler in a hardenable resin to form a paste. High loading levels of the acid-reactive filler in the paste (e.g., 70% by weight or higher) are often desired to provide high strength and durability of the pastes after hardening, high radiopacity, as well as high levels of fluoride release. However, loading higher levels of acid-reactive filler in the paste may result in a paste with less desirable properties (e.g., Theological properties). For example, high loadings of acid-reactive filler may result in pastes with poor handling and/or mixing characteristics (e.g., hard, dry, stringy, high viscosity, difficult to mix, and/or difficult to spread), each of which may make the use of such pastes by dental practitioners undesirable.

As such, there remains a need in the art for acid-reactive fillers with improved properties. For example, acid-reactive fillers that may be incorporated into resins at high loading levels to provide pastes, while maintaining the rheological properties typical for pastes with lower loading levels of known acid-reactive fillers (e.g., low viscosity, easily dispensed and mixed) are sought.

SUMMARY OF THE INVENTION

In one aspect, the present invention provides a dental paste including a hardenable resin and an acid-reactive filler disposed in the resin, wherein the filler includes a silane-treated surface, and wherein the silane includes a poly(alkylene oxide) group-containing silane. Preferably, the acid-reactive filler is fluoroaluminosilicate glass. Optionally, the paste includes a fatty acid.

In another aspect, the present invention provides a method of preparing a dental paste. The method includes combining an acid-reactive filler including a silane-treated surface with a hardenable resin, wherein the silane includes a poly(alkylene oxide) group-containing silane.

In another aspect, the present invention provides a method of lowering the viscosity of a dental paste including a hardenable resin and an acid-reactive filler. The method includes contacting the acid-reactive filler with a composition preparable by combining components including a medium and a poly(alkylene oxide) group-containing silane. Preferably the medium includes water. Optionally the medium is acidic or basic.

In another aspect, the present invention provides a kit including a part A and a part B. Part A includes (i) an acid-reactive filler including a silane-treated surface, wherein the silane includes a poly(alkylene oxide) group-containing silane; and (ii) a fatty acid. Part B includes at least one polyacid. The kit further includes a resin and an initiator, each independently residing in Part A and/or Part B. Preferably, the kit further including a dual barrel syringe having a first barrel and a second barrel, where the part A resides in the first barrel and the part B resides in the second barrel. Methods of using the kit are also provided.

In another aspect, the present invention provides a dental article including a hardened resin and an acid-reactive filler disposed in the hardened resin. The filler includes a silane-treated surface, wherein the silane includes a poly(alkylene oxide) group-containing silane. Methods of preparing dental articles are also provided.

In another aspect, the present invention provides an acid-reactive filler including a silane-treated surface, wherein the silane includes a poly(alkylene oxide) group-containing silane. Optionally, the silane further includes a silane that does not contain a poly(alkylene oxide) group. Preferably, the acid-reactive filler is a fluoroaluminosilicate glass. Methods of preparing the a surface-treated, acid-reactive filler are also provided.

Definitions

As used herein, the term "paste" refers to a soft, viscous mass of solids disposed or incorporated into liquid.

As used herein, "filler" means a particulate material (e.g., an inorganic oxide) capable of being incorporated into a resin. For example, a dental composite preferably includes a powder disposed in a resin.

As used herein, an "acid-reactive filler" refers to fillers that, when contacted with acid, undergo a chemical reaction. Examples of acid-reactive fillers include, for example, metal oxides, metal salts, and glasses. As used herein, a "glass" refers to an amorphous, hard, and generally brittle material. Preferred glasses include those that release fluoride upon contact with acid. A particularly preferred fluoride-releasing glass in fluoroaluminosilicate (FAS) glass.

As used herein, a "fluoroaluminosilicate glass" refers to fluoride-releasing glasses as described, for example, in U.S. Pat. No. 3,655,605 (Smith et al.), U.S. Pat. No. 3,814,717 (Wilson et al.), U.S. Pat. No. 4,043,327 (Potter et al.), U.S. Pat. No. 4,143,018 (Crisp et al.), U.S. Pat. No. 4,209,434 (Wilson et al.), and U.S. Pat. No. 5,063,257 (Akahane et al.).

As used herein, the term "silane treated" means that the surface of a particle has been modified by contacting a composition prepared by combining components including the silane and/or silanol. The silane and/or silanol may optionally be in a medium, and the silane and/or silanol may react or be transformed in the composition before or during the treatment of the surface of the particle.

As used herein, the term "poly(alkylene oxide) group" means a group that includes at least two, and preferably from 2 to 30, alkylene oxide units. Preferred alkylene oxides include, for example, ethylene oxide, propylene oxide, butylene oxide, and combinations thereof.

As used herein, "hardenable" is descriptive of a material that can be cured or solidified, e.g., by heating to remove solvent, heating to cause polymerization, chemical crosslinking, radiation-induced polymerization or crosslinking, or the like.

As used herein, "fatty acid" refers to a saturated or unsaturated organic compound including an aliphatic group, preferably containing 4 to 22 carbon atoms, and characterized by a terminal carboxylic acid group.

As used herein, the term "aliphatic group" means a saturated or unsaturated linear (i.e., straight chain), cyclic, or branched hydrocarbon group. This term is used to encompass alkyl (e.g., —CH$_3$) (or alkylene if within a chain such as —CH$_2$—), alkenyl (or alkenylene if within a chain), and alkynyl (or alkynylene if within a chain) groups, for example. The term "alkyl group" means a saturated linear or branched hydrocarbon group including, for example, methyl, ethyl, isopropyl, t-butyl, heptyl, dodecyl, octadecyl, amyl, 2-ethylhexyl, and the like. The term "alkenyl group" means an unsaturated, linear or branched hydrocarbon group with one or more carbon-carbon double bonds, such as a vinyl group. The term "alkynyl group" means an unsaturated, linear or branched hydrocarbon group with one or more carbon-carbon triple bonds. The term "aromatic group" or "aryl group" means a mono- or polynuclear aromatic hydrocarbon group. These hydrocarbon groups may be substituted with heteroatoms, which can be in the form of functional groups, if so stated. The term "heteroatom" means an element other than carbon (e.g., nitrogen, oxygen, sulfur, chlorine, etc.).

As used herein, "consistency value" refers to a measure of the flow characteristics of a material, with higher numbers indicating higher flow out or lower viscosity. In brief, the consistency value is a measure of the diameter of a sample of a material that has been flattened between two glass plates under the conditions specified herein.

DETAILED DESCRIPTION OF PREFERRED EMBODIMENTS

In one embodiment, the present invention provides a dental paste including a hardenable resin and an acid-reactive filler disposed in the resin. The acid-reactive filler includes a silane-treated surface, wherein the silane includes a poly(alkylene oxide) group-containing silane. An initiator may be included in, or added to, the hardenable resin to effect hardening of the resin. In some embodiments, the paste may also include a fatty acid.

Acid-Reactive Filler

Suitable acid-reactive fillers include metal oxides, metal salts and glasses. Preferred metal oxides include barium oxide, calcium oxides magnesium oxide and zinc oxide. Preferred metal salts include salts of multivalent cations, for example aluminum acetate, aluminum chloride, calcium chloride, magnesium chloride, zinc chloride, aluminum nitrate, barium nitrate, calcium nitrate, magnesium nitrate, strontium nitrate and calcium fluoroborate. Preferred glasses include borate glasses, phosphate glasses and fluoroaluminosiicate glasses. Fluoroaluxninosilicate glasses are particularly preferred. Suitable fillers are also availabie from a variety of commercial sources familiar to those skilled in the art. For example, suitable fillers can be obtained from a number of commercially available glass jonomer cements, such as "(GC Fuji LC" cement and "Kerr XR" ionomer cement. Mixtures of fillers can be used if desired.

Suitable acid-reactive fillers include, for example, metal oxides, metal salts, and glasses. Of these, glasses are preferred. Suitable metal oxides and metal salts are disclosed, for example, in U.S. Pat. No. 5,154,762 (Mitra et al.) at column 3, lines 55 to 62. Suitable glasses include, for example, borate glasses, phosphate glasses, and fluoroaluminosilicate (FAS) glasses, which are particularly preferred. The FAS glasses are described, for example, in U.S. Pat. No. 3,655,605 (Smith et al.); U.S. Pat. No. 3,814,717 (Wilson et al.); U.S. Pat. No. 4,043,327 (Potter et al.); U.S. Pat. No. 4,143,018 (Crisp et al.); U.S. Pat. No. 4,209,434 (Wilson et al.); and U.S. Pat. No. 5,063,257 (Akahane et al.). The glass preferably contains leachable fluoride to provide useful protection against dental caries. Preferably, the glass is sufficiently finely divided to provide easy mixing, rapid cure, and good handling properties. Any convenient pulverizing or comminuting methods can be used to make finely divided glasses. Ball-milling is one exemplary approach.

Silane and/or Silanol Treatment

Preferably, the acid-reactive fillers are silane and/or silanol treated by methods similar to those described, for example, in U.S. Pat. No. 5,332,429 (Mitra et al.). In brief, the acid-reactive fillers described above can be treated by contacting them with a composition including a poly(alkylene oxide) group-containing silane, optionally in a medium. If a medium is included, preferably the medium includes water, and if an aqueous medium is used, it can be acidic or basic. Once treated, the acid-reactive filler can be dried using any convenient technique. Oven drying in a forced air oven is recommended, with drying temperatures of about 30° to about 100° C. being preferred. Preferably drying is carried out overnight. The treated and dried acid-reactive filler can then be screened or lightly comminuted to break up agglomerates. The resulting acid-reactive filler can be incorporated, for example, into a dental paste.

Preferably, the alkylene of the poly(alkylene oxide) group of the silane includes ethylene, propylene, butylene, and combinations thereof. Preferably, the poly(alkylene oxide) group-containing silane has the formula:

$$X_nSi\text{—}(\text{—}Y\text{—}(OC_mH_{2m})_w\text{—}Z)_{4-n}$$

wherein X is a hydrolyzable group (e.g., alkoxy, acyloxy, halo, or combinations thereof); Y is a saturated or unsaturated, substituted or unsubstituted, aliphatic and/or aromatic group, which may optionally include heteroatoms (e.g., O, N, S, P, and combinations thereof that may be present as functional groups including, for example, ethers, sulfides, esters, carbamates, and amides); Z is a saturated or unsaturated, aliphatic and/or aromatic group, which may optionally include heteroatoms (e.g., O, N, S, P, and combinations thereof that may be present as functional groups including, for example, ethers, sulfides, esters, carbamates, and amides); m=2–4; n=1–3 (preferably 3); and w=2–30. Preferred Z groups include, for example, methoxy, ethoxy, acryloxy, methacryloxy, and vinyl ethers.

Suitable poly(alkylene oxide) group-containing silanes are known in the art and include, for example, gamma-(polyalkylene oxide)propyltrimethoxysilane available under the trade designation A1230 from OSI Specialties, Danbury, Conn. Other suitable poly(alkylene oxide) group-containing silanes include, for example, those including a urethane group, which may be obtained, for example, by reacting an isocyanate functional silane (e.g., 2-isocyanotriethyltriethoxysilane available under the trade designation A1310 from OSI Specialties, Danbury, Conn.; and 3-(triethoxysilyl) propyl isocyanate available from Aldrich Chemical Co., Milwaukee, Wis.) with end capped polyalkylene glycols. Examples of such poly(alkylene oxide) group-containing silanes are disclosed in the working examples of the present application.

In some embodiments, the present invention provides a dental paste that includes a hardenable resin and an acid-reactive filler disposed in the resin, wherein the filler includes a silane-treated surface, and wherein the silane includes a poly(alkylene oxide) group-containing silane and a silane that does not contain a poly(alkylene oxide) group. Silanes that do not contain a poly(alkylene oxide) group may be either polymerizable or non-polymerizable. Combinations of polymerizable and non-polymerizable silanes may also be used.

Examples of silanes that do not contain a poly(alkylene oxide) group and that are not polymerizable include isooctyltrimethoxysilane, phenyltrimethoxysilane, n-octyltrimethoxysilane, dodecyltrimethoxysilane, octadecyltrimethoxysilane, propyltrimethoxysilane, hexyltrimethoxysilane, 3-mercaptopropyltrimethoxysilane, 3-aminopropyltrimethoxysilane, 3-gylcidoxypropyltrimethoxysilane, and combinations thereof.

Examples of polymerizable silanes that do not contain a poly(alkylene oxide) group include 3-(methacryloxy)propyltrimethoxysilane, 3-acryloxypropyltrimethoxysilane, 3-(methacryloxy)propyltriethoxysilane, 3-(methacryloxy)propylmethyldimethoxysilane, 3-(acryloxypropyl)methyldimethoxysilane, 3-(methacryloxy)propyldimethylethoxysilane, 3-(methacryloxy)methyltriethoxysilane, 3-(methacryloxy)methyltrimethoxysilane, 3-(methacryloxy)propyldimethylethoxysilane, 3-methacryloxypropenyl trimethoxysilane, vinyldimethylethoxysilane, vinylmethyldiacetoxysilane, vinylmethyldiethoxysilane, vinyltriacetoxysilane, vinyltriethoxysilane, vinyltriisopropoxysilane, vinyltrimethoxysilane, vinyltriphenoxysilane, vinyltri-t-butoxysilane, vinyl-tris-isobutoxysilane, vinyltriisopropenoxysilane, vinyl-tris(2-methoxyethoxy)silane, and combinations thereof. Of these, 3-(methacryloxy)propyltrimethoxysilane, 3-acryloxypropyltrimethoxysilane, 3-(methacryloxy)propylmethyldimethoxysilane, and 3-(methacryloxy)propyldimethylethoxysilane are preferred.

According to the surface treatment method for FAS glass filler described in U.S. Pat. No. 5,332,429 (Mitra et al.), the silanol treatment solution may be adjusted with an acid or a base to yield a non-neutral solution. Optionally, at least one silane that is acid- or base-functionalized may be used. The surface treatment is done in the presence of water. Accordingly, the silane(s) may be converted to silanol(s). The acid or base and the silanol react with the FAS glass. See column 2, lines 5 to 13. The resulting surface treated FAS glass is an acid-reactive fluoroaluminosilicate particulate glass having an ion-containing, siloxy-containing coating.

Fatty Acid

Pastes of the present invention may include a fatty acid as an additive. In other words, the fatty acid is not pre-coated on the acid-reactive fillers. The phrase "fatty acid," as used herein means an organic compound including an aliphatic group, preferably containing 4 to 22 carbon atoms, and characterized by a terminal carboxylic group. Dimers and trimers of the fatty acid, preferably containing 4 to 22 carbon atoms per carboxyl group, can also be used in the present invention. The fatty acid can be saturated or unsaturated. When fatty acids are present, pastes of the present invention preferably include at least about 0.01% by weight, and more preferably at least about 0.1% by weight fatty acid, based on the total weight of the paste. When fatty acids are present, pastes of the present invention preferably include at most about 5% by weight, and more preferably at most about 1% by weight fatty acid, based on the total weight of the paste.

Useful fatty acids include, for example, the fatty acids of caprylic acid ($CH_3(CH_2)_6CO_2H$), capric acid ($CH_3(CH_2)_8CO_2H$), octadecanoic acid ($CH_3(CH_2)_{16}COOH$), commonly referred to as stearic acid, and 9-octadecenoic acid ($CH_3(CH_2)_7CH:CH(CH_2)_7COOH$), commonly referred to as oleic acid. Particularly useful fatty acids are oleic acid and its dimer and trimer.

Hardenable Resins

Dental pastes of the present invention include a hardenable resin. These resins preferably are generally thermosetting materials capable of being hardened to form a polymer network including, for example, acrylate-functional materials, methacrylate-functional materials, epoxy-functional materials, vinyl-functional materials, and mixtures thereof. Preferably, the hardenable resin is made from one or more matrix-forming oligomer, monomer, polymer, or blend thereof.

In a preferred embodiment where the dental paste disclosed in the present application is a dental composite, polymerizable materials suitable for use include hardenable organic materials having sufficient strength, hydrolytic stability, and non-toxicity to render them suitable for use in the oral environment. Examples of such materials include acrylates, methacrylates, urethanes, carbamoylisocyanurates, epoxies, and mixtures and derivatives thereof.

One class of preferred hardenable materials includes materials having free radically active functional groups. Examples of such materials include monomers having one or more ethylenically unsaturated group, oligomers having one or more ethylenically unsaturated group, polymers having one or more ethylenically unsaturated group, and combinations thereof. Alternatively, the hardenable resin can be selected from materials that include cationically active functional groups. In another alternative, a mixture of hardenable resins that include both cationically curable and free radically curable materials may be used for the dental materials of the invention. In another alternative, the hardenable resin can be a material from the class of materials that includes both cationically active and free radically active functional groups in the same molecule.

Free Radically Active Materials. In the class of hardenable resins having free radically active functional groups, suitable materials for use in the invention contain at least one ethylenically unsaturated bond, and are capable of undergoing addition polymerization. Such free radically polymerizable materials include mono-, di- or poly-acrylates and methacrylates such as methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, the diglycidyl methacrylate of bisphenol A ("Bis-GMA"), bis[1-(2-acryloxy)]-p-ethoxyphenyldimethylmethane, bis[1-(3-acryloxy-2-hydroxy)]-p-propoxyphenyldimethylmethane, and trishydroxyethylisocyanurate trimethacrylate; the bis-acrylates and bis-methacrylates of polyethylene glycols of molecular weight 200–500, copolymerizable mixtures of acrylated monomers such as those in U.S. Pat. No. 4,652,274 (Boettcher et al.), and acrylated oligomers such as those of U.S. Pat. No. 4,642,126 (Zador); and vinyl compounds such as styrene, diallyl phthalate, divinyl succinate, divinyl adipate and divinylphthalate. Mixtures of two or more of these free radically polymerizable materials can be used if desired.

Free Radical Initiation Systems. For free radical polymerization (e.g., hardening), an initiation system can be selected from systems that initiate polymerization via radiation, heat, or redox/auto-cure chemical reaction. A class of initiators capable of initiating polymerization of free radically active functional groups includes free radical-generating photoinitiators, optionally combined with a photosensitizer or accelerator. Such initiators typically can be capable of generating free radicals for addition polymerization upon exposure to light energy having a wavelength between 200 and 800 nm.

A variety of visible or near-IR photoinitiator systems may be used for photopolymerization of free-radically polymerizable materials. For example, a photoinitiation system can be selected from systems which initiate polymerization via a two component system of an amine and an α-diketone as described in U.S. Pat. No. 4,071,424 (Dart et al.). Alternatively, the material can be combined with a three component photoinitiator system such as described in U.S. Pat. No. 5,545,676 (Palazzotto et al.). The three component system includes an iodonium salt (e.g., a diaryliodonium salt), a sensitizer, and a donor. Each photoinitiator component is described in U.S. Pat. No. 5,545,676 (Palazzotto et al.), column 2, line 27, to column 4, line 45.

Other useful free-radical initiators include the class of acylphosphine oxides, as described in European Pat. Application Publ. No. 173,567 (Ying) and U.S. Pat. No. 4,737,593 (Ellrich et al.) and U.S. Pat. No. 6,020,528 (Leppard et al.). Tertiary amine reducing agents may be used in combination with an acylphosphine oxide.

Another free-radical initiator system that can alternatively be used in the dental materials of the invention includes the class of ionic dye-counterion complex initiators including a borate anion and a complementary cationic dye. Borate salt photoinitiators are described, for example, in U.S. Pat. No. 4,772,530 (Gottschalk et al.), U.S. Pat. No. 4,954,414 (Adair et al.), U.S. Pat. No. 4,874,450 (Gottschalk), U.S. Pat. No. 5,055,372 (Shanklin et al.), and U.S. Pat. No. 5,057,393 (Shanklin et al.).

Yet another alternative class of initiators capable of initiating polymerization of free radically active functional groups in the hardenable resin includes conventional chemical initiator systems such as a combination of a peroxide and an amine. These initiators, which rely upon a thermal redox reaction, are often referred to as "auto-cure catalysts." They are typically supplied as two-part systems in which the reactants are stored apart from each other and then combined immediately prior to use.

In a further alternative, heat may be used to initiate the hardening, or polymerization, of free radically active groups. Examples of heat sources suitable for the dental materials of the invention include inductive, convective, and radiant. Thermal sources should be capable of generating temperatures of at least about 40° C. and at most about 150° C. under normal conditions or at elevated pressure. This procedure is preferred for initiating polymerization of materials occurring outside of the oral environment.

Yet another alternative class of initiators capable of initiating polymerization of free radically active functional groups in the hardenable resin are those that include free radical-generating thermal initiators. Examples include peroxides (e.g., benzoyl peroxide and lauryl peroxide) and azo compounds (e.g., 2,2-azobis-isobutyronitrile (AIBN)).

Cationically Active Materials. An alternative class of hardenable resins useful in dental pastes disclosed in the present application includes materials having cationically active functional groups. Materials having cationically active functional groups include cationically polymerizable epoxies (e.g., those shown in U.S. Pat. No. 3,066,112 (Bowen), U.S. Pat. No. 3,539,533 (Lee II et al.), U.S. Pat. No. 3,629,187 (Waller), U.S. Pat. No. 3,709,866 (Waller), U.S. Pat. No. 3,751,399 (Lee et al.), U.S. Pat. No. 3,766,132 (Lee et al.), U.S. Pat. No. 3,860,556 (Taylor), U.S. Pat. No. 4,002,669 (Gross et al.), U.S. Pat. No. 4,115,346 (Gross et al.), U.S. Pat. No. 4,259,117 (Yamauchi et al.), U.S. Pat. No. 4,292,029 (Craig et al.), U.S. Pat. No. 4,308,190 (Walkowiak et al.), U.S. Pat. No. 4,327,014 (Kawahara et al.), U.S. Pat. No. 4,379,695 (Orlowski et al.), U.S. Pat. No. 4,387,240 (Berg), U.S. Pat. No. 4,404,150 (Tsunekawa et al.)), vinyl ethers, oxetanes, spiro-orthocarbonates, spiro-orthoesters, and the like. Preferred materials having cationically active functional groups are epoxy-functional materials including, for example, those disclosed in U.S. Pat. No. 6,025,406 (Oxman et al.) (e.g., column 2, line 36 to column 4, line 52) and in the documents cited therein.

Optionally, monohydroxy- and polyhydroxy-alcohols may be added to the hardenable resin, as chain-extenders for a hardenable resin having cationically active functional groups, which are preferably epoxy-functional materials. The hydroxyl-containing material used in the present invention can be any organic material having hydroxyl functionality of at least about 1, and preferably at least about 2. Useful hydroxyl-containing materials are described, for example, in U.S. Pat. No. 5,856,373 (Kaisaki et al.).

For hardening resins including cationically active functional groups, an initiation system can be selected from systems that initiate polymerization via radiation, heat, or redox/auto-cure chemical reactions. For example, epoxy polymerization may be accomplished by the use of thermal curing agents including, for example, anhydrides and amines. A particularly useful example of an anhydride curing agent is cis-1,2-cyclohexanedicarboxylic anhydride.

Alternatively, initiation systems for resins including cationically active functional groups are those that are photoactivated. The broad class of cationic photoactive groups recognized in the catalyst and photoinitiator industries may be used in the practice of the present invention. Photoactive cationic nuclei, photoactive cationic moieties, and photoactive cationic organic compounds are art recognized classes of materials as exemplified by, for example, U.S. Pat. No. 4,250,311 (Crivello); U.S. Pat. No. 3,708,296 (Schlesinger); U.S. Pat. No. 4,069,055 (Crivello); U.S. Pat. No. 4,216,288 (Crivello); U.S. Pat. No. 5,084,586 (Farooq); U.S. Pat. No. 5,124,417 (Farooq); U.S. Pat. No. 4,985,340 (Palazzotto et al.), U.S. Pat. No. 5,089,536 (Palazzotto), and U.S. Pat. No. 5,856,373 (Kaisaki et al.).

The cationically-curable materials can be combined with a three component or ternary photoinitiator system, as described above, for example, using an iodonium salt, a sensitizer, and an electron donor. For hardening cationically curable materials, examples of useful aromatic iodonium complex salts are disclosed in U.S. Pat. No. 6,025,406 (Oxman et al.) (e.g., column 5, line 46, to column 6, line 9). Examples of useful sensitizers and electron donors can also be found in U.S. Pat. No. 6,025,406 (Oxman et al.) (e.g., column 6, line 43, to column 9, line 43).

An alternative photoinitiator system for cationic polymerizations includes the use of organometallic complex cations essentially free of metal hydride or metal alkyl functionality selected from those described in U.S. Pat. No. 4,985,340 (Palazzotto et al.).

Cationically Active/Free Radically Active Materials. Alternatively, the hardenable resins may have both cationically active and free radically active functional groups contained in a single molecule. Such molecules may be obtained, for example, by reacting a di- or poly-epoxide with one or more equivalents of an ethylenically unsaturated carboxylic acid. An example of such a material is the reaction product of a material, which is available under the trade designation UVR-6105 from Union Carbide, with one equivalent of methacrylic acid. Commercially available materials having epoxy and free-radically active functionalities include materials available under the trade designation CYCLOMER (e.g., CYCLOMER M-100, M-101, or A-200) from Daicel Chemical, Japan, and the material available under the trade designation EBECRYL-3605 from Radcure Specialties.

Photoinitiator compounds are preferably provided in dental pastes disclosed in the present application in an amount effective to initiate or enhance the rate of cure or hardening of the resin system. Useful photopolymerizable compositions are prepared by simply admixing, under safe light conditions, the components as described above. Suitable inert solvents may be used, if desired, when preparing this mixture. Any solvent that does not react appreciably with the components of the inventive compositions may be used. Examples of suitable solvents include, for example, acetone, dichloromethane, and acetonitrile. A liquid material to be polymerized may be used as a solvent for another liquid or solid material to be polymerized. Solventless compositions can be prepared, for example, by simply dissolving an aromatic iodonium complex salt and sensitizer in an epoxy-functional material/polyol mixture with or without the use of mild heating to facilitate dissolution.

Other Additives

The inventive dental pastes may optionally include adjuvants suitable for use in the oral environment including, for example, colorants, flavorants, anti-microbials, fragrances, stabilizers, viscosity modifiers, and fluoride releasing materials. For example, suitable adjuvants include agents that impart fluorescence and/or opalescence.

Pastes of the present invention can further include a viscosity modifier such as a hydrogen-bondable polymer having a number average molecular weight greater than about 10,000. Preferably, the polymer has a number average molecular weight greater than about 20,000, and more preferably greater than about 50,000. Generally, this polymer is present in a small amount of the total composition. Preferably, the polymer is present in the paste at about 0.05% to 8% by weight, more preferably at about 0.1% to 5% by weight, based on the resin component in the paste. Preferably, the hydrogen-bondable polymer includes hydrogen-bond acceptor sites.

Particularly preferred hydrogen-bondable polymers include, for example, poly(N-vinylpyrrolidone) polymers (p-NVP). Copolymers of vinylpyrrolidone and other monomers or grafted poly(N-vinylpyrrolidone) with other groups also are preferred, provided that the co-monomers or grafting groups do not contain an adverse amount of active hydrogens for hydrogen bonding. For example, poly(1-vinylpyrrolidone-co-styrene), polyethyloxazoline, poly(1-vinylpyrrolidone-co-vinyl acetate), and combinations thereof, are preferred.

Optionally, compositions of the present invention may also include fumed silica. Suitable fumed silicas include for example, products available under the trade designations AEROSIL OX-50, AEROSIL-130, AEROSIL-150, and AEROSIL-200 available from DeGussa AG, (Hanau, Germany) and CAB-O-SIL M5 available from Cabot Corp (Tuscola, Ill.).

Incorporation of Fillers into Resins

Fillers disclosed in the present application may be incorporated into a hardenable resin by any suitable means to form a dental paste. Surface treated acid-reactive fillers may be added to the resin as a powder. Alternatively, the surface treated acid-reactive filler may be combined with another filler and/or optional additives to provide a material that is then added to the hardenable resin as a powder. Alternatively, the surface treated acid-reactive filler may be combined with liquid additives and added to the hardenable resin as a dispersion.

The fillers disclosed in the present application may be incorporated into the hardenable resin by any convenient method known in the art.

Dental Pastes

Surface treated acid-reactive fillers disclosed in the present application can be incorporated into a hardenable resin to provide useful dental pastes as described above. Dental pastes of the present invention can be chemically curable, heat curable, or light curable compositions. Light curable materials should have an appropriate initiator system. Chemically curable materials can be auto-cure (e.g. via redox initiators). Alternatively, the materials of the invention can be hardened by a combination of auto- and light-cure.

Dental pastes disclosed in the present application include an acid-reactive filler disposed in the resin, wherein the filler includes a silane-treated surface, and wherein the silane includes a poly(alkylene oxide) group-containing silane. Preferably the dental paste includes at least about 5% by weight of the surface treated acid-reactive filler and more preferably at least about 10% by weight of the surface treated acid-reactive filler, based on the total weight of the paste. Preferably the dental paste includes at most about 85% by weight of the surface treated acid-reactive filler, more preferably at most about 80% by weight of the surface treated acid-reactive filler, based on the total weight of the paste.

The dental pastes disclosed in the present application can be used, for example, as dental adhesives, artificial crowns, anterior or posterior fillings, casting materials, cavity liners, cements, coating compositions, mill blanks, orthodontic devices, restoratives, prostheses, and sealants. In a preferred aspect, the dental paste is a dental restorative. The restoratives of the invention can be placed directly in the mouth and cured (hardened) in situ, or alternatively, may be fabricated into a prosthesis outside the mouth and subsequently adhered in place inside the mouth.

It has been found that dental pastes of the invention, although filled at relatively high filler levels still possess useful rheological properties (e.g., soft, non-sticky). These properties as well as strength are believed to be enhanced by the use of surface-modifying agents to treat the surface of the particles. Surface treatment (surface-modification) enhances the dispersibility of the particles and their ability to bind into the matrix.

Preferably, the present invention provides dental pastes that are capable of being hardened to provide a balance of desirable properties as detailed below (e.g., a high diametral tensile strength, a high compressive strength, and a high adhesion value) while retaining excellent handling and Theological properties (e.g., no substantial settling after 5 days of storage at about 25° C., and a consistency value of at least about 30 mm). Preferably, the dental paste is non-sticky when handled using well known procedures by one of skill in the art.

Kit Including Part A and Part B

In one embodiment, the invention provides a kit that includes a two-part (e.g., a part A and a part B) glass ionomer cement. The viscosity of part A is typically greater than about 50,000 centipoise (cps), preferably between 150,000 to 300,000 cps when measured at or near room temperature (about 25° C.) using a Brookfield viscometer using a T-D spindle with a conversion factor equal to 32,000. Typically, a dental practitioner mixes the two parts immediately prior to use. As the two parts are mixed, an acid-base hardening reaction begins. Preferably the mixture has a working time, as defined in the test procedure herein, of at least about 30 seconds, and more preferably at least about 60 seconds. Subsequent hardening of the ethylenically-unsaturated groups or the curable resin is done by curing agents and/or by light. Each component used to formulate parts A and B are discussed in detail herein. Certain components such as the hardenable resin and the initiator may reside in either part A, part B, or both Part A and Part B as further explained below.

In one embodiment, the dental pastes disclosed in the present invention may be used as a Part A in a glass ionomer cement. Such pastes include an acid-reactive filler disposed in the resin, wherein the filler includes a silane-treated surface, and wherein the silane includes a poly(alkylene oxide) group-containing silane. When used as a Part A in a glass ionomer cement, the paste preferably includes at least about 50% by weight of the surface treated acid-reactive filler, more preferably at least about 60% by weight of the surface treated acid-reactive filler, and most preferably at least about 70% by weight of the acid-reactive filler, based on the total weight of the paste. When used as a Part A in a glass ionomer cement, the paste preferably includes at most about 85% by weight of the surface treated acid-reactive filler, and more preferably at most about 80% by weight of the surface treated acid-reactive filler, based on the total weight of the paste.

Part B contains at least one polyacid, which may be a hardenable (e.g., curable) resin or a non-hardenable (e.g., non-curable) resin. The polyacid need not be entirely water soluble, but it should be at least sufficiently water-miscible so that it does not undergo substantial sedimentation when combined with other components of Part B. Suitable polyacids are listed in U.S. Pat. No. 4,209,434 (Wilson et al.), column 2, line 62, to column 3, line 6. The polyacid should have a molecular weight sufficient to provide good storage, handling, and mixing properties. A preferred weight average molecular weight is about 5,000 to 100,000, evaluated against a polystyrene standard using gel permeation chromatography.

In one embodiment, the polyacid is a hardenable resin. That is, it contains at least one ethylenically unsaturated group. Suitable ethylenically unsaturated polyacids are described in U.S. Pat. No. 4,872,936 (Engelbrecht), e.g., at columns 3 and 4, and EP 323 120 B1 (Mitra), e.g., at about page 3, line 55, to page 5, line 8. Preferably, the numbers of acidic groups and ethylenically unsaturated groups are adjusted to provide an appropriate balance of properties in the dental composition. Polyacids in which about 10% to 30% of the acidic groups have been replaced with ethylenically unsaturated groups are preferred.

In other embodiments, the polyacid is non-hardenable resin. That is, it is an oligomer or polymer of an unsaturated acid. Preferably, the unsaturated acid is an oxyacid (i.e., an oxygen containing acid) of carbon, sulfur, phosphorous, or boron. More preferably, it is an oxyacid of carbon. Useful non-hardenable polyacids include, for example, polyalkenoic acids such as homopolymers and copolymers of unsaturated mono-, di-, or tricarboxylic acids. Preferred polyalkenoic acids can be prepared by the homopolymerization and copolymerization of unsaturated aliphatic carboxylic acids, e.g., acrylic acid, 2-choloracrylic acid, 3-choloracrylic acid, 2-bromoacrylic acid, 3-bromoacrylic acid, methacrylic acid, itaconic acid, maleic acid, glutaconic acid, aconitic acid, citraconic acid, mesaconic acid, fumaric acid, and tiglic acid. Suitable monomers that can be copolymerized with the unsaturated aliphatic carboxylic acids include, for example, unsaturated aliphatic compounds such as acrylamide, acrylonitrile, vinyl chloride, allyl chloride, vinyl acetate, and 2-hydroxyethyl methacrylate. Ter- and higher polymers may be used if desired. Particularly preferred are the homopolymers and copolymers of acrylic acid. The polyalkenoic acid should be substantially free of unpolymerized monomers.

The amount of polyacid in the dental composition, whether hardenable or non-hardenable resin, should be sufficient to provide a desired balance of properties. Part B preferably includes at least about 10% by weight of the polyacid and more preferably at least about 30% by weight of the polyacid, based on the total weight of Part B. Part B preferably includes at most about 70% by weight of the polyacid and more preferably at most about 60% by weight of the polyacid, based on the total weight of Part B.

Part B also contains water, which can be present in the product as sold or added by the dental practitioner just prior to use. The water can be distilled, deionized (DI), or tap water, with deionized water being preferred. Just prior to use, the total dental composition preferably includes at least about 1% by weight water, more preferably at least about 3% by weight water, and most preferably at least about 5% by weight water. Just prior to use, the total dental composition preferably includes at most about 35% by weight water, and more preferably at most about 25% by weight water. In general, the amount of water used should be sufficient to provide adequate handling and mixing properties for the dental composition and to permit the transport of ions in the acid-reactive filler-polyacid reaction, particularly the treated FAS glass-polyacid reaction.

Hardened Dental Compositions

Dental pastes disclosed in the present application including an acid-reactive filler disposed in the resin, wherein the filler includes a silane-treated surface, and wherein the silane includes a poly(alkylene oxide) group-containing silane, have especially desirable handling (e.g., Theological) properties in an unhardened state and high strength in a hardened state.

Strength can be characterized by mechanical measurements such as compressive strength (CS) and diametral tensile strength (DTS). High compressive strength in a dental material is advantageous due to the forces exerted by mastication on dental repairs, replacements and restorations. Diametral tensile strength indicates the dental material's ability to withstand compression forces that introduce a tensile stress in the material. Tests for each strength measurement are set out below in the Examples.

The dental pastes disclosed in the present application, when hardened, preferably have a compressive strength of at least about 60 MPa; more preferably, a compressive strength of at least about 80 MPa; and most preferably, a compressive strength of at least about 90 MPa. Hardened dental pastes of the invention preferably have a diametral tensile strength of at least about 10 MPa; more preferably at least about 15 MPa; and most preferably at least about 20 MPa.

Dental Articles

The pastes of the present invention may be hardened to form, for example, dental articles. In a preferred method of using dental pastes including a hardenable resin and fillers as disclosed in the present application, the paste may be placed near or on a tooth surface, followed by a manipulation by the practitioner or laboratory to change the topography of the paste, then the resin may be hardened. These steps can be followed sequentially or in a different order. For example, in a preferred embodiment where the dental material is a mill blank or a prosthesis, the hardening step is generally completed prior to changing the topography of the paste. Changing the topography of the paste can be accomplished in various ways including, for example, carving or manual manipulation using hand held instruments, or by machine or computer aided apparatus (e.g., a CAD/CAM milling machine) in the case of prostheses and mill blanks. Optionally, a finishing step can be performed to polish, finish, or apply a coating on the dental material.

EXAMPLES

The following examples are provided to illustrate different embodiments and details of the invention. Although the examples serve this purpose, the particular ingredients and amounts used as well as other conditions and details are not to be construed in a manner that would unduly limit the scope of this invention. Unless otherwise specified, all percentages are in weight percent. Table 1 below is used for convenience and lists the components used in the Examples below.

TABLE 1

Abbreviations and Sources of Materials

| Components | Description |
|---|---|
| A1230 | gamma-(polyalkylene oxide)propyltrimethoxysilane (OSI Specialties, Danbury, CT) |
| A174 | gamma-methacryloxypropyltrimethoxysilane (OSI Specialties, Danbury CT) |
| Octyl Silane | octyltrimethoxy silane (Aldrich Chemical Co., Milwaukee, WI) |
| BHT | 2,6-di-tert-butyl-4-methylphenol |
| CPQ | camphorquinone |
| DPIPF6 | diphenyl iodonium hexafluorophosphate |
| FAS glass | fluoroaluminosilicate glass G018-091 (Schott Glass, Westborough, MA) |
| Fujibond LC | GC Fuji Bond LC Standard Set (GC Corp., Tokyo, Japan) |
| HEMA | 2-hydroxyethylmethacrylate |
| bisGMA | 2,2-bis[4-(2-hydroxy-3-methacryloyloxy-propoxy)phenyl]propane |
| TEGDMA | triethyleneglycol dimethacrylate (Sartomer Co., Exton, PA) |
| oleic acid | 9-octadecenoic acid |
| dimer acid | dimer of 9-octadecenoic acid, EMPOL 1008 (Cognis, Canterbury, CT) |
| MFPA | methacrylated functional polycarboxylic acid, made according to Ex. 11 of U.S. Pat. No. 5,130,347 (Mitra) |
| p-NVP | polyvinyl pyrrolidone (Plasdone K-25; 38,000 $M_n$) (ISP Technologies Inc., Wayne, NJ) |
| S/T FAS | treated FAS glass, treated with silanol or silane |
| DI Water | deionized water |
| | di(ethylene glycol) methyl ether (Aldrich Chemical Co., Milwaukee, WI) |
| MEK | methylethylketone (Aldrich Chemical Co., Milwaukee, WI) |
| MEHQ | p-methoxyphenol (Aldrich Chemical Co., Milwaukee, WI) |
| | 3-(triethoxysilyl)propyl isocyanate (Aldrich Chemical Co., Milwaukee, WI) |
| | dibutyl tin dilaurate (Aldrich Chemical Co., Milwaukee, WI) |
| | tri(ethylene glycol) methyl ether (Aldrich Chemical Co., Milwaukee, WI) |

TABLE 1-continued

Abbreviations and Sources of Materials

| Components | Description |
|---|---|
| | poly(ethylene glycol) methyl ether, MW350 (Aldrich Chemical Co., Milwaukee, WI) |
| | di(ethylene glycol) mono vinyl ether (BASF, Parsippany, NJ) |
| | poly(propyleneglycol) methacrylate, MW = 350–389 (Aldrich Chemical Co., Milwaukee, WI) |

Diametral Tensile Strength and Compressive Strength Testing

ADA (American Dental Association) specification No. 9 and ADA specification No. 27 respectively of ISO-test procedure 4049 (1988) were followed for all diametral tensile strength (DTS) and compressive strength (CS) testing. Specifically for CS and DTS, the composition was packed into a 4 mm inside diameter glass tube. The tube was capped with silicone rubber plugs and axially compressed at about 0.28 MPa, then light cured for 60 seconds by exposure to two oppositely-disposed dental curing light units available under the trade designations Visilux 2 from 3M, St. Paul, Minn. Each sample was then irradiated for 90 seconds using a unit available under the trade designation Dentacolor XS from Kulzer, Inc., Germany. Cured samples were cut on a diamond saw to form cylindrical plugs of 4 mm in diameter and 8 mm long for CS testing and 2 mm long for DTS testing. The samples were stored in distilled water at 37° C. for 24 hours ±2 hours. CS and DTS values for each composition were measured using a unit available under the trade designation Instron 4505 from Instron Corp., Canton, Mass. The CS testing used a 10 kN load cell and a total of 3 to 5 cylinders were tested The DTS testing was also done with 10 kN load cell and a total of 6 to 8 cylinders were tested.

Adhesive Testing

Adhesive strength to dentin for the Examples below was evaluated by the following procedure. For each example, seven bovine teeth of similar age and appearance were partially embedded in circular acrylic discs. The exposed portion of each tooth was ground flat and parallel to the flat surface of acrylic disc using Grade 120 silicon carbide paper-backed abrasive mounted on a lapidary wheel. This grinding step exposed the dentin. During all grinding and polishing steps, the teeth were continuously rinsed with water. Further grinding and polishing of the teeth was carried out by mounting Grade 600 silicon carbide paper-backed abrasive on the lapidary wheel.

The polished teeth were stored in deionized water and used for testing within 2 hours after polishing. The polished teeth were removed from the water and blotted dry. To produce an even thickness of the Examples for testing, a small square piece of 3M Adhesive tape (Core Series 2–1300, 3M, St. Paul, Minn.), with a hole of 4.76 mm diameter making a "tape hole," was placed on top of the slightly moist dentin. The final dimensions of the tape hole were 0.03 mm in thickness by 4.76 mm in diameter. The adhesive side of the tape hole was placed over the slightly moist dentin. The paste and liquid components (i.e., parts A and B respectively) for each Example and Comparative Example were dispensed from a dispenser available under the trade designation 3M CLICKER from 3M, St. Paul, Minn., onto a mixing pad and mixed for 10 to 15 seconds.

A brush or ball applicator was used to transfer the formulation into the tape hole. A curing light available under the trade designation Visilux 2 was used to cure the composition for 30 seconds and the tape hole was removed to expose the cured formulation. Adhesion testing molds were made from a 2-mm thick sheet available under the trade designation TEFLON from E. I. DuPont de Nemours, Wilmington, Del. The final dimensions of the mold were 4.76 mm in diameter and 2 mm in thickness. The mold was lined with gelatin and clamped securely on top of the cured formulation in line with the tape hole. A Z-100, A3 shade composite (3M, St. Paul, Minn.) was compressed into the mold and light cured for 40 sec with a curing light available under the trade designation Visilux 2. The test sample was immediately placed in deionized water and aged for 24 hours at 37° C. The molds were then carefully removed from the teeth, leaving a molded button of the cured inventive formulation attached to each tooth.

The strength of the cured inventive formulation was evaluated by mounting the acrylic disk in a holder clamped in the jaws of a unit available under the trade designation Instron 4505 with the polished tooth surface oriented parallel to the direction of pull. A loop of orthodontic wire (0.44 mm diameter) was placed around the cured sample adjacent to the polished tooth surface. The ends of the orthodontic wire were clamped in the pulling jaw of the Instron apparatus, thereby placing the bond in shear stress. The bond was stressed until it (or the dentin or the formulation) failed, using a crosshead speed of 2 mm per minute.

Settling Test

A 20 g sample for part A in Table 3 below of each Example and Comparative Example was stored at room temperature (about 25° C.) in a 75 ml plastic jar having a diameter of 3.8 cm. Phase separation, as indicated by the formation of a transparent liquid layer on the top of the sample, was checked daily by visual inspection. After five days, all of the examples were visually inspected and evaluated for the formation of a transparent layer. A dental mixing stick was used to collect the clear liquid, which was then spread over the top of a glass microscope slide. The liquid on glass slide was visually inspected for transparency and the presence of FAS particles.

Working Time Test

The paste (part A in Table 3) and liquid (part B in Table 4) parts of each example were filled into a dispenser available under the trade designation 3M CLICKER. Two clicks of example material were dispensed onto a mixing pad. Using a stainless steel spatula or dental mixing stick, the two-part formulation was mixed together. Timing began at the start of mixing and ended when the mixed formulation became stringy and tacky between the spatula and mixing pad. The time interval was recorded in seconds.

Consistency Value Measurement

A known amount of paste was placed between two glass plates with additional weight on top. The weight was allowed to flatten the samples for 120 seconds. Then the weight was removed and the flow out was measured by the diameter of the paste between the glass plates. A larger resultant diameter (i.e., a larger flow out) indicated a lower paste viscosity. Pastes were weighed (0.15 g +/−0.005 g) on the center of a 10.16 cm×10.16 cm (4 inch×4 inch) glass plate. The plate was placed in a jig, which allowed the weight to be applied to the center of the plate. The top 10.16 cm×10.16 cm (4×4 in) plate and weight were applied (total weight 1027 g). The weight was applied for 120 sec. The diameter was measured and reported in millimeters (mm).

Silanol Treatment of FAS Glass

A 300 ml beaker with a flat bottom was used as a reaction vessel to prepare the silanol treatment on a fluoroaluminosilicate (FAS) glass. The beaker was equipped with a conventional mixing device, such as a magnetic stirrer. A 100 g portion of deionized water was weighed into the beaker and approximately 0.9 g of glacial acetic acid was added to the water. The solution was stirred for 5 to 10 minutes at a speed fast enough to create a small vortex. The pH of the solution was measured at 2.5 to 3.0 with pH paper.

The silanes, A-174 and/or A-1230, were added to the solution in the amounts as indicated in Table 2 for Examples 1 to 6 and Comparative Examples A and B. While adding the indicated amount of silane into the solution, the solution appeared oily and slightly hazy. The silane-water-acid solution was stirred with a small vortex for 1 hour to hydrolyze. After 1 hour, a clear solution was obtained.

A 100 g portion of FAS glass was added into the solution to create a slurry. The glass was added gradually in 5 minutes with stirring. After all the glass was added, the slurry was stirred for an additional 30 minutes. The silanol treated FAS glass slurry was transferred to clean plastic trays for drying. The silanol treated glass was dried for 14 hours at 80° C. in a drying oven. The dried cake was screened through a 74 mm screen to yield silanol treated FAS glass (S/T FAS) for the study.

TABLE 2

Materials Used for Silanol Treated FAS Glass used in Paste Examples

| FAS Glass used in Example | DI H$_2$O (g) | FAS glass (g) | A 1230 (g) | A 174 (g) |
|---|---|---|---|---|
| 1 | 100 | 100 | 2 | 2 |
| 2 | 100 | 100 | 3 | 1 |
| 3 | 100 | 100 | 4 | 0 |
| 4 | 100 | 100 | 2 | 2 |
| 5 | 100 | 100 | 3 | 1 |
| 6 | 100 | 100 | 4 | 0 |
| Comp. A | 100 | 100 | 0 | 4 |
| Comp. B | 100 | 100 | 0 | 4 |
| Comp. C | 100 | 100 | 0 | 0 |
| Comp. D | 100 | 100 | 0 | 0 |

Examples 1 To 6 and Comparative Examples A–D

These examples were made as a two-part formulation. Part A was made by mixing the components listed in Table 3. Any convenient mixing method may be used, but ordinarily the resin components of HEMA, bisGMA and p-NVP, were thoroughly mixed followed by adding the FAS glass and oleic acid components to the resin mixture. The FAS glass used in Comparative Examples C and D was not previously treated with silanol. All of the components of Part A were then thoroughly mixed. Part B was made by mixing the components listed in Table 4. The two-part formulation was loaded into a dispenser available under the trade designation 3M CLICKER from 3M, St. Paul, Minn. An equal volume amount of each part was dispensed onto a mixing pad and thoroughly mixed for 10 to 15 seconds to yield the dental composition. Each composition was tested for the various properties listed in Table 5.

TABLE 3

Materials and Amounts For Part A (g)

| Part A used in Ex. | HEMA | bis-GMA | p-NVP | S/T FAS | oleic acid | dimer acid |
|---|---|---|---|---|---|---|
| 1 | 19.86 | 6.62 | 0.27 | 73 | 0.25 | 0 |
| 2 | 19.86 | 6.62 | 0.27 | 73 | 0.25 | 0 |
| 3 | 19.86 | 6.62 | 0.27 | 73 | 0.25 | 0 |
| 4 | 19.67 | 6.56 | 0.27 | 73 | 0 | 0.25 |
| 5 | 19.67 | 6.56 | 0.27 | 73 | 0 | 0.25 |
| 6 | 19.67 | 6.56 | 0.27 | 73 | 0 | 0.25 |
| Comp. A | 19.86 | 6.62 | 0.27 | 73 | 0.25 | 0 |
| Comp. B | 19.67 | 6.56 | 0.27 | 73 | 0 | 0.25 |
| Comp. C | 20.04 | 6.69 | 0.27 | 73* | 0 | 0 |
| Comp. D | 20.04 | 6.59 | 0.27 | 73* | 0 | 0.25 |

*FAS glass without silanol treatment

TABLE 4

Materials and Amounts for Part B (g)

| Components | Amount |
|---|---|
| MFPA | 43.00 |
| DI H$_2$O | 39.25 |
| HEMA | 16.45 |
| CPQ | 0.63 |
| DPIPF6 | 0.63 |
| BHT | 0.04 |

TABLE 5

Physical Properties

| Example | Settling for Part A | Working time* | DTS (MPa) | CS (MPa) | Adhesion (MPa) |
|---|---|---|---|---|---|
| 1 | No | 110 | 18.14 | 122.07 | 9.03 |
| 2 | No | 110 | 19.79 | 115.86 | 9.18 |
| 3 | No | 115 | 14.90 | 109.66 | 11.29 |
| 4 | No | 115 | 18.41 | 120.69 | 10.49 |
| 5 | No | 115 | 20.55 | 106.90 | 10.34 |
| 6 | No | 115 | 14.07 | 98.62 | 9.54 |
| Comp. A | n/a | n/a | 19.58 | 107.58 | 9.03 |
| Comp. B | n/a | n/a | 21.51 | 116.55 | 9.18 |
| Comp. C | Yes | <15 | n/a | n/a | 7.14 |
| Comp. D | No | <15 | n/a | n/a | 5.61 |
| Fujibond LC | ND** | 90 | 21.03 | 141.38 | 6.76 |

*±10 seconds
**ND not done as formulation is a powder and liquid
n/a is not available as samples were not tested After 5 days of storage, Comp. Example C had formed a separated and transparent liquid layer phase.

As the data in Table 5 indicates, Examples 1 to 6, all of which embody the invention, showed no settling and had adequate working time. They also exhibited acceptable DTS, CS, and adhesion to dentin.

Comparative Example C, however, had settling of the filler, and too short of a working time. Its adhesion to dentin was also lower than those of Examples 1 to 6. Although Comparative Example D showed no settling, its working time was short and had lower adhesion to dentin, compared to Examples 1 to 6. The Fujibond LC sample was a powder-liquid system and such disadvantages have been discussed above. It did have adequate DTS and CS, but showed slightly lower adhesion to dentin, as compared to Examples 1 to 6.

Example 7

Fluoroaluminosilicate (FAS) glass was surface treated according to the procedure described herein, except that a combination of DI water and ethanol were used for samples that included octyl silane. DI water/ethanol was acidified with glacial acetic acid to a pH of about 2.5 to 3.0 before the surface treatment. The materials and quantities used in the surface treatment procedures are listed in Table 6.

TABLE 6

Materials Used for Silanol Treated FAS Glass

| S/T FAS Sample Number | DI H$_2$O (g) | Ethanol | FAS Glass (g) | A174 (g) | A1230 (g) | Octyl Silane (g) |
|---|---|---|---|---|---|---|
| 20 | 100 | 0 | 100 | 4 | 0 | 0 |
| 21 | 100 | 0 | 100 | 3 | 1 | 0 |
| 22 | 100 | 0 | 100 | 2 | 2 | 0 |
| 23 | 100 | 0 | 100 | 1 | 3 | 0 |
| 24 | 100 | 0 | 100 | 0 | 4 | 0 |
| 25 | 70 | 70 | 100 | 3 | 0 | 1 |
| 26 | 70 | 70 | 100 | 2 | 0 | 2 |
| 27 | 70 | 70 | 100 | 1 | 0 | 3 |
| 28 | 70 | 70 | 100 | 0 | 0 | 4 |
| 29 | 70 | 70 | 100 | 0 | 1 | 3 |
| 30 | 70 | 70 | 100 | 0 | 2 | 2 |
| 31 | 70 | 70 | 100 | 0 | 3 | 1 |

Pastes were prepared from each of the samples of S/T FAS glass fillers by mixing the fillers into a resin mixture prepared by mixing the components HEMA (19.86), bis-GMA (6.62), and p-NVP (0.27) in the indicated ratios by weight as described in the preparation of Part A in Examples 1–6, to provide pastes with the filler at 73% solids (by weight).

The rheological and/or handling properties of the pastes were evaluated by manually manipulating the pastes and then ranking the pastes on a scale of 1 (worst) to 5 (best), with a score of 1 corresponding to a thick paste having a high viscosity (e.g., similar in viscosity to a dough) that will not flow on its own, and a score of 5 corresponding to a soft, low viscosity paste or pourable liquid (e.g., similar in viscosity to a syrup or gravy) that will flow on its own. The results are listed in Table 7.

TABLE 7

Physical Properties of Pastes

| S/T FAS Sample Number | Comments | Score* |
|---|---|---|
| 20 | Stringy, low viscosity | 2.5–3 |
| 21 | Low viscosity | 4.5 |
| 22 | Low viscosity | 4.5 |
| 23 | Low viscosity | 5 |
| 24 | Low viscosity | 5 |
| 25 | Thick, high viscosity | 2 |
| 26 | Thick, high viscosity | 2 |
| 27 | Thick, high viscosity | 2 |
| 28 | Thick, high viscosity | 2 |
| 29 | Thick, high viscosity | 2 |
| 30 | Thick, high viscosity | 2 |
| 31 | Low-medium viscosity, stringy | 4.5 |

*from 1 (worst) to 5 (best)

The above results show that the surface treatment of the FAS filler has a significant effect on the rheology of the pastes prepared therefrom.

Additional pastes were prepared from samples 20–24 of S/T FAS glass fillers by mixing the fillers into the resin mixture as described above, except that oleic acid (0.25% by weight) was also added to provide pastes with the filler at 73% solids (by weight). The rheological and/or handling properties of these pastes were evaluated by manually manipulating the pastes and then ranking the pastes on a scale of 1 (worst) to 5 (best), with a score of 1 corresponding to a thick paste having a high viscosity (e.g., similar in viscosity to a dough), and a score of 5 corresponding to a soft, smooth, paste having a low to medium viscosity (e.g., similar in viscosity to shaving cream or frosting). The results are listed in Table 8.

TABLE 8

Physical Properties of Pastes

| S/T FAS Sample Number | Score* |
|---|---|
| 20 | 3 |
| 21 | 3.5 |
| 22 | 4 |
| 23 | 4.5 |
| 24 | 4.5–5 |

*from 1 (worst) to 5 (best)

The above results show that the surface treatment of the FAS filler has a significant effect on the rheology of the pastes prepared therefrom.

Additional pastes were prepared from samples 20 and 23 of S/T FAS glass fillers by mixing the fillers into a mixture of the following resins (parts by weight): HEMA (79.21), bisGMA (17.82), TEGDMA (1.98), and p-NVP (0.99). Pastes of each surface treated filler were prepared with the filler being at 70%, 74%, 76%, and 80% by weight of the paste. The flow properties of these pastes were determined by measurement of the consistency values of the pastes, and the results are listed in Table 9.

TABLE 9

Consistency Values of Pastes

| S/T FAS Sample Number | Filler (wt %) | Consistency Value (mm) |
|---|---|---|
| 23 | 70 | 49 |
| 23 | 74 | 44 |
| 23 | 76 | 41 |
| 23 | 80 | 32 |
| 20 | 70 | 41 |
| 20 | 74 | 38 |
| 20 | 76 | 33 |
| 20 | 80 | 11 |

The above results indicate that the surface treatment of the FAS filler has a significant effect on the flow properties of the pastes prepared therefrom.

Example 8

Preparation of a Poly(Alkylene Oxide) Group-containing Silane by Reaction of Di(Ethylene Glycol) Methyl Ether with 3-(Triethoxysilyl)Propyl Isocyanate A 250 ml round bottom flask equipped with a magnetic stir bar was charged with di(ethylene glycol) methyl ether (35 g) and methylethylketone (77 g). A majority of the solvent was removed via rotary evaporation to remove water. 3-(Triethoxysilyl)propyl isocyanate (68.60 g) was charged to the flask. Dibutyltin dilaurate (~3 mg) was added, and the mixture was stirred. The reaction proceeded with a mild exotherm. The reaction was run for approximately 16 hours at which time infrared (IR) spectroscopy showed no isocyanate. The remainder of the solvent and alcohol were removed via rotary evaporation (90° C.) to yield a somewhat viscous liquid (104.46 g).

Example 9

Preparation of a Poly(Alkylene Oxide) Group-containing Silane by Reaction of Tri(Ethylene Glycol) Methyl Ether with 3-(Triethoxysilyl)Propyl Isocyanate This compound was made by a similar procedure to that for the PEG2TES except tri(ethylene glycol) methyl ether was used instead of di(ethylene glycol) methyl ether.

Example 10

Preparation of a Poly(Alkylene Oxide) Group-containing Silane by Reaction of Di(Ethylene Glycol) Vinyl Ether with 3-(Triethoxysilyl)Propyl Isocyanate A 50 ml round bottom flask equipped with a magnetic stir bar was charged with di(ethylene glycol) vinyl ether (12.06 g) and methylethylketone (15 g). A majority of the solvent was removed via rotary evaporation to remove water. 3-(Triethoxysilyl)propyl isocyanate (20.17 g) was charged to the flask. Dibutyltin dilaurate (~3 mg) was added, and the mixture was stirred. The reaction proceeded with a mild exotherm. The reaction was run for approximately 16 hours at which time IR spectroscopy showed no isocyanate. The remainder of the solvent and alcohol were removed via rotary evaporation (90° C.) to yield a somewhat viscous liquid.

Example 11

Preparation of a Poly(Alkylene Oxide) Group-containing Silane by Reaction of a Poly(Ethyleneglycol) Methyl Ether with 3-(Triethoxysilyl)Propyl Isocyanate A 250 ml round bottom flask equipped with a magnetic stir bar was charged with poly(ethyleneglycol) methyl ether (MW=350) (18.34 g) and methylethylketone (48.8 g). The solvent (25 g) was removed via distillation. 3-(Triethoxysilyl)propyl isocyanate (12.5 g) was charged to the flask. Dibutyltin dilaurate (~3 mg) was added, and the mixture was stirred. The reaction proceeded with a mild exotherm. The reaction was run for approximately 4 hours with mild heating at which time IR spectroscopy showed no isocyanate. The remainder of the solvent was removed via rotary evaporation.

Example 12

Preparation of a Poly(Alkylene Oxide) Group-containing Silane by Reaction of a Poly(Propyleneglycol) Methacrylate with 3-(Triethoxysilyl)Propyl Isocyanate A 200 ml round bottom flask equipped with a magnetic stir bar was charged with poly(propyleneglycol) methacrylate (MW=350-389) (25.11 g), MEHQ (0.11 g) and methylethylketone (62 g). The solvent (40 g) was removed via rotary evaporation. 3-(Triethoxysilyl)propyl isocyanate (15.95 g) was charged to the flask. Dibutyltin dilaurate (~3 mg) was added, and the mixture was stirred. The reaction mixture was heated to 45° C. (6 hr) and further reacted at room temperature for approximately 12 hours at which time IR spectroscopy showed no isocyanate. The remainder of the solvent was removed via rotary evaporation.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A composition comprising
a hardenable resin; and
an acid-reactive filler disposed in the resin, wherein the filler is selected from the group consisting of metal oxides, metal salts, glasses, and mixtures thereof, wherein the filler comprises a silane-treated surface, wherein the silane comprises a poly(alkylene oxide) group-containing silane, wherein the composition is a dental paste, and wherein the paste forms a material selected from the group consisting of dental restoratives, dental adhesives, casting materials, dental cements, dental sealants, and dental coatings.

2. The composition of claim 1 wherein the acid-reactive filler is selected from the group consisting of metal oxides, glasses, and combinations thereof.

3. A composition comprising:
a hardenable resin; and
an acid-reactive filler disposed in the resin, wherein the acid-reactive filler is a glass selected from the group consisting of borate glasses, phosphate glasses, and fluoroaluminosilicate glasses, wherein the filler comprises a silane-treated surface, wherein the silane comprises a poly(alkylene oxide) group-containing silane, and wherein the composition is a dental paste.

4. The composition of claim 3 wherein the acid-reactive filler is a fluoroaluminosilicate glass.

5. The composition of claim 4 wherein the paste comprises at least about 5% by weight of the fluoroaluminosilicate glass.

6. The composition of claim 4 wherein the paste further comprises a fatty acid.

7. The composition of claim 6 wherein the fatty acid is selected from the group consisting of caprylic acid and/or dimers thereof, capric acid and/or dimers thereof, stearic acid and/or dimers thereof, oleic acid and/or dimers thereof, and combinations thereof.

8. The composition of claim 1 wherein the alkylene of the poly(alkylene oxide) group is selected from the group consisting of ethylene, propylene, butylene, and combinations thereof.

9. The composition of claim 8 wherein the poly(alkylene oxide) group-containing silane has the formula:

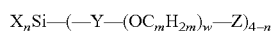

wherein X is a hydrolyzable group; Y is a saturated or unsaturated, substituted or unsubstituted, aliphatic and/or aromatic group, which may optionally include heteroatorms; Z is a saturated or unsaturated, aliphatic and/or aromatic group, which may optionally include heteroatoms; m=2–4; n=1–3; and w=2–30.

10. A composition comprising:
a hardenable resin; and
an acid-reactive filler disposed in the resin, wherein the filler is selected from the group consisting of metal oxides, metal salts, glasses, and mixtures, wherein the filler comprises a silane-treated surface, wherein the silane comprises a poly(alkylene oxide) group-containing silane and a silane that does not contain a poly(alkylene oxide) group, and wherein the composition is a dental paste.

11. The composition of claim 10 wherein the silane that does not contain a poly(alkylene oxide) group is selected from the group consisting of isooctyltrimethoxysilane, phenyltrimethoxysilane, n-octyltrimethoxysilane, dodecyltrimethoxysilane, octadecyltrimethoxysilane, propyltrimethoxysilane, hexyltrimethoxysilane, 3-mercaptopropyltrimethoxysilane, 3-aminopropyltrimethoxysilane, 3-gylcidoxypropyltrimethoxysilane, and combinations thereof.

12. The composition of claim 10 wherein the silane that does not contain a poly(alkylene oxide) group comprises a polymerizable functionality.

13. The composition of claim 12 wherein the silane that does not contain a poly(alkylene oxide) group is selected from the group consisting of 3-(methacryloxy)propyltrinethoxysilane, 3-acryloxypropyltrimethoxysilane, 3-(methacryloxy)propyltriethoxysilane, 3-(methacryloxy)propylmethyldimethoxysilane, 3-(acryloxypropyl)methyldimethoxysilane, 3-(methacryloxy)propyldimethylethoxysilane, 3-(methacryloxy)methyltriethoxysilane, 3-(methacryloxy)methyltrimethoxysilane, 3(methacryloxy)propyldimethylethoxysilane, 3-methacryloxypropenyl trimethoxysilane, vinyldimethylethoxysilane, vinylmethyldiacetoxysilane, vinylmethyldiethoxysilane, vinyltriacetoxysilane, vinyltriethoxysilane, vinyltriisopropoxysilane, vinyltrimethoxysilane, vinyltriphenoxysilane, vinyltri-t-butoxysilane, vinyl-tris-isobutoxysilane, vinyltriisopropenoxysilane, vinyl-tris(2-methoxyethoxy)silane, and combinations thereof.

14. The composition of claim 4 wherein the paste is free of fatty acid and comprises at least about 70% by weight of the fluoroaluminosilicate glass filler and the paste has a consistency value of at least about 35 mm.

15. The composition of claim 4 wherein the paste is free of fatty acid and comprises at least about 74% by weight of the fluoroaluminosilicate glass filler and the paste has a consistency value of at least about 30 mm.

16. The composition of claim 4 wherein the paste is free of fatty acid and comprises at least about 76% by weight of the fluoroaluminosilicate glass filler and the paste has a consistency value of at least about 25 mm.

17. The composition of claim 4 wherein the paste is free of fatty acid and comprises at least about 80% by weight of the fluoroaluminosilicate glass filler and the paste has a consistency value of at least about 20 mm.

18. A composition comprising:
a hardenable resin;
an acid-reactive filler disposed in the resin; and
a fatty acid,
wherein the acid-reactive filler is a fluoroalumnnosilicate glass, wherein the filler comprises a silane-treated surface, wherein the silane comprises a poly(alkylene oxide) group-containing silane, and wherein the composition is a dental paste that exhibits no substantial settling after 5 days of storage at about 25° C.

19. The composition of claim 1 wherein the hardenable resin is selected from the group consisting of acrylates, methacrylates, epoxies, and combinations thereof.

20. The composition of claim 1 further comprising an initiator.

21. The composition of claim 1 wherein the paste exhibits one or more properties selected from the group consisting of no substantial settling after 5 days of storage at about 25° C., and a consistency value of at least about 30 mm.

22. The composition of claim 1 wherein the paste, upon hardening, has one or more properties selected from the group consisting of: a diametral tensile strength of at least about 10 MPa, a compressive strength of at least about 80 MPa, and an adhesion value of at least about 4 MPa.

23. A method of preparing a composition comprising combining an acid-reactive filler selected from the group consisting of metal oxides, metal salts, glasses, and mixtures thereof, and comprising a silane-treated surface with a hardenable resin to form a dental paste, wherein the silane comprises a poly(alkylene oxide) group-containing silane, and wherein the paste forms a material selected from the group consisting of dental restoratives, dental adhesives, casting materials, dental cements, dental sealants, and dental coatings.

24. A method of lowering the viscosity of a dental paste comprising a hardenable resin and an acid-reactive filler selected from the group consisting of metal oxides, metal salts, glasses, and mixtures thereof, the method comprising contacting the acid-reactive filler with a composition preparable by combining components comprising a medium and a poly(alkylene oxide) group-containing silane, to form a dental paste comprising a filler having a silane-treated surface.

25. The method of claim 24 wherein the medium comprises water.

26. The method of claim 24 wherein the medium is acidic or basic.

27. A kit comprising:
a part A comprising:
  (i) an acid-reactive filler comprising a silane-treated surface, wherein the silane comprises a poly(alkylene oxide) group-containing silane; and
  (ii) a fatty acid; and
a part B comprising at least one polyacid,
wherein the kit further comprises a resin and an initiator, each independently residing in Part A and/or Part B.

28. The kit of claim 27 further comprising a dual barrel syringe having a first band and a second barrel, wherein the part A resides in the first barrel and the part B resides in the second barrel.

29. A method of using the kit of claim 27 comprising:
dispensing a quantity of part A and a quantity of part B onto a mixing pad;
mixing the quantity of part A and the quantity of part B together to form a dental composition; and
applying the dental composition to a dental structure.

30. The method of claim 29 wherein the dental composition has a working time of at least about 30 seconds.

31. The method of claim 30 wherein the dental composition has a working time of at least about 60 seconds.

32. An article comprising:
a hardened resin; and
an acid-reactive filler disposed in the hardened resin, wherein the filler is selected from the group consisting of metal oxides, metal salts, glasses, and mixtures wherein the filler comprises a silane-treated surface, wherein the silane comprises a poly(alkylene oxide) group-containing silane, and wherein the article is a dental article.

33. The article of claim 32 wherein the article is selected from the group consisting of dental mill blanks, dental prostheses, orthodontic devices, artificial crowns, anterior fillings, posterior fillings, and cavity liners.

34. The article of claim 32 having one or more properties selected from the group consisting of: a diametral tensile strength of at least about 10 MPa, a compressive strength of at least about 80 MPa, and an adhesion value of at least about 4 MPa.

35. A method of preparing a dental article comprising:
dispersing an acid-reactive filler in a hardenable resin to form a dental paste, wherein the filler is selected from the group consisting of metal oxides, metal salts, glasses, and mixtures thereof, wherein the filler comprises a silane-treated surface, and wherein the silane comprises a poly(alkylene oxide) group-containing silane; and
hardening the paste to fabricate a dental article selected from the group consisting of dental mill blanks, dental prostheses, orthodontic devices, artificial crowns, anterior fillings, posterior fillings, and cavity liners.

36. The method of claim 35 further comprising changing the topography of the paste before hardening the dental paste.

37. An acid-reactive filler selected from the group consisting of metal oxides, metal salts, glasses, and mixtures thereof, and comprising a silane-treated surface, wherein the silane comprises a poly(alkylene oxide) group-containing silane and a silane that does not contain a poly(alkylene oxide) group.

38. An acid-reactive filler comprising a silane-treated surface, wherein the acid-reactive filler is a fluoroaluminosilicate glass, and wherein the silane comprises a poly(alkylene oxide) group-containing silane and a silane that does not contain a poly(alkylene oxide) group.

39. A method of preparing a surface-treated acid-reactive filler comprising:
combining components comprising a medium, a poly(alkylene oxide) group-containing silane, and a silane that does not contain a poly(alkylene oxide) group, to provide a surface-treatment composition; and
contacting the surface treatment composition with the acid-reactive filler, wherein the filler is selected from the group consisting of metal oxides, metal salts, glasses, and mixtures thereof.

40. A dental paste comprising:
a hardenable resin; and
an acid-reactive filler disposed in the resin, wherein the filler is selected from the group consisting of metal oxides, metal salts, glasses, and mixtures thereof, wherein the filler comprises a silane-treated surface, and wherein the silane comprises a poly(alkylene oxide) group-containing silane and a silane that does not contain a poly(alkylene oxide) group.

* * * * *

UNITED STATES PATENT AND TRADEMARK OFFICE
CERTIFICATE OF CORRECTION

PATENT NO. : 7,091,259 B2
APPLICATION NO. : 10/190321
DATED : August 15, 2006
INVENTOR(S) : Hoa T. Bui et al.

It is certified that error appears in the above-identified patent and that said Letters Patent is hereby corrected as shown below:

On the Title Page item (57), Column 2:
Line 1-9, Delete "The present invention provides a dental paste, methods of making and using the dental paste, and compositions prepared therefrom. The dental paste includes (a) a filler including porous, non-pyrogenic silica having a silane treated surface and being substantially free of heavy metals and (b) a filler including non-agregated primary silica particles, with the fillers being dispersed in a hardenable resin. Fillers including porous, non-pyrogenic silica, and methods of making and using the fillers, are also provided." and insert -- The present invention provides a dental paste, methods of making and using the dental paste, and compositions prepared therefrom. The dental paste includes a hardenable resin and an acid-reactive filler disposed in the resin. The acid-reactive filler includes a silane-treated surface, wherein the silane includes a poly(alkylene oxide) group-containing silane. --, therefor.

Page 2, Column 1:
Line 2, After "6,376,590" delete "B1" and insert -- B2 --, therefor.

Page 2, Column 2:
Line 5, After "Sheet," delete "OSi" and insert -- OSI --, therefor.

Column 1:
Line 9, Delete "fluoroalumuniosilicate" and insert -- fluoroaluminosilicate --, therefor.
Line 34, Delete "Theological" and insert -- rheological --, therefor.

Column 2:
Line 27, After "the" delete "a".

Column 3:
Line 48, After "calcium" delete "oxides" and insert -- oxide, --, therefor.
Line 54-55, Delete "fluoroaluminosiicate" and insert -- fluoroaluminosilicate --, therefor.
Line 55, Delete "Fluoroaluxninosilicate" and insert -- Fluoroaluminosilicate --, therefor.
Line 56, Delete "availabie" and insert -- available --, therefor.
Line 59, Delete "jonomer" and insert -- ionomer --, therefor.
Line 60, After "such as" delete ""(GC" and insert -- "GC --, therefor.

UNITED STATES PATENT AND TRADEMARK OFFICE
CERTIFICATE OF CORRECTION

PATENT NO. : 7,091,259 B2
APPLICATION NO. : 10/190321
DATED : August 15, 2006
INVENTOR(S) : Hoa T. Bui et al.

It is certified that error appears in the above-identified patent and that said Letters Patent is hereby corrected as shown below:

Column 10:
Line 63, Delete "Theological" and insert -- rheological --, therefor.

Column 12:
Line 48, Delete "Theological)" and insert -- rheological) --, therefor.

Column 14:
Line 36, After "tested" insert -- . --.

Column 21:
Line 18, In Claim 1, after "comprising" insert -- : --.
Line 64-65, In Claim 9, delete "heteroatorns;" and insert -- heteroatoms; --, therefor.

Column 22:
Line 5, In Claim 10, delete "mixtures," and insert -- mixtures thereof, --, therefor.
Line 25-26, In Claim 13, delete "3 (methacryloxy)propyltriinethoxysilane," and insert -- 3 (methacryloxy)propyltrimethoxysilane, --, therefor.
Line 32, In Claim 13, delete "3(methacryloxy)" and insert -- 3-(methacryloxy) --, therefor.
Line 62, In Claim 18, delete "fluoroalumnnosilicate" and insert -- fluoroaluminosilicate --, therefor.

Column 23:
Line 48, In Claim 28, delete "band" and insert -- barrel --, therefor.

UNITED STATES PATENT AND TRADEMARK OFFICE
CERTIFICATE OF CORRECTION

PATENT NO. : 7,091,259 B2
APPLICATION NO. : 10/190321
DATED : August 15, 2006
INVENTOR(S) : Hoa T. Bui et al.

It is certified that error appears in the above-identified patent and that said Letters Patent is hereby corrected as shown below:

Column 24:
Line 1, In Claim 32, delete "mixtures" insert -- mixtures thereof, --.

Signed and Sealed this

Twenty-third Day of June, 2009

JOHN DOLL
*Acting Director of the United States Patent and Trademark Office*